(12) United States Patent
Aubart et al.

(10) Patent No.: US 6,617,357 B2
(45) Date of Patent: Sep. 9, 2003

(54) COMPOUNDS AND THEIR USE AS PDE INHIBITORS

(75) Inventors: Kelly M. Aubart, Collegeville, PA (US); Siegfried B. Christensen, IV, Collegeville, PA (US); Jack D. Leber, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/683,897

(22) Filed: Feb. 28, 2002

(65) Prior Publication Data

US 2002/0156064 A1 Oct. 24, 2002

Related U.S. Application Data

(60) Provisional application No. 60/273,649, filed on Mar. 6, 2001.

(51) Int. Cl.[7] .................................................. A61K 31/18
(52) U.S. Cl. ........................................ 514/602; 564/84
(58) Field of Search ............................ 514/602; 564/84

(56) References Cited

U.S. PATENT DOCUMENTS 4,025,538 A * 5/1977 Lutz et al.

OTHER PUBLICATIONS

Yo et al. Chem. Pharm. Bull. (Tokyo) (1964), 12(1), 5–13 CAS ABSTRAT*

* cited by examiner

*Primary Examiner*—Joseph K. McKane
*Assistant Examiner*—Kamal Saeed
(74) *Attorney, Agent, or Firm*—James M. Kanagy; Charles M. Kinzig

(57) ABSTRACT

This invention relates to certain benzenesulfonamides and their use as PDE7 inhibitors.

4 Claims, No Drawings

COMPOUNDS AND THEIR USE AS PDE INHIBITORS

BACKGROUND OF INVENTION

This invention relates to certain benzenesulfonamides and their use as PDE7 inhibitors.

Cyclic nucleotide phosphodiesterases (PDEs) represent a family of enzymes that hydrolyze the ubiquitous intracellular second messengers, adenosine 3',5'-monophosphate (cAMP) and guanosine 3',5'-monophosphate (cGMP) to their corresponding inactive 5'-monophosphate metabolites. At least 14 distinct classes of PDE isozymes are believed to exist, each possessing unique physical and kinetic characteristics and each representing a product of a different gene family. These are distinguished using Arabic numerals 1–14. And within each distinct class; there may be two or more distinct sub-types. See reviews by Crocker, I et al, Drugs Today, 35(7), 519–535 (1999), Fawcett, L. et al, PNAS, 97(7), 3702–3703 (2000) and Yuasa, K et al, J Biol Chem., 275(40), 31496–31479 (2000).

The present invention relates to the PDE isozyme which is currently identified as PDE7 or HCP1-PDE. This type 7 isozyme is found in various tissues and in particularly high concentrations in skeletal muscle. Two sub-types have been identified, PDE7A Michaeli, T, et al, J Biol Chem., 268 (17) 12925–12932 (1993); Han, P et al, J Biol Chem. 272(26), 16152–16157 (1997) and PDE7B; U.S. Pat. No. 6,146,876; Gardner, C. et al, Biochem Biophys Res. Commun. 272 (1) 186–192 (2000); and Saski, T. et al, Biochem Biophys Res Commun. 271 (3), 575–583 (2000). Herein these will be referred to collectively as PDE7 unless otherwise stated.

PDE7 inactivates secondary messenger cAMP by hydrolysis and inhibition of PDE7 results in increased levels of cAMP. Inhibition of PDE7 may be useful in the treatment of asthma, rheumatoid arthritis, psoriasis, atopic dermatitis and chronic bronchitis. While assessment of PDE7 message expression indicates a broad cellular distribution, PDE7 protein expression and activity is localized mostly to T-lymphocytes and lymphoid tissue. Consequently, PDE7 inhibitors may be useful in the treatment of T-cell-mediated disorders. Morerover, selective PDE7 inhibitors may have reduced adverse events sometimes encountered with other PDE inhibitors, events such as CNS, GI and cardiovascular side effects.

SUMMARY OF INVENTION

This invention relates to compounds of Formula 1 for use in the mediation or inhibition of the enzymatic activity (or catalytic activity) of PDE7 in mammals, including humans, which comprises administering to a mammal in need thereof an effective amount of a compound of Formula 1:

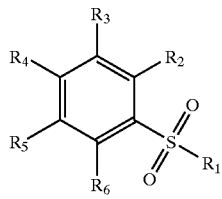

wherein,
$R_1$ is $NR_aR_b$ where $R_a$ and $R_b$ are independently H or $C_{1-6}$ alkyl, or —$NR_aR_b$ represents a 5 to 7 member ring comprised of carbon or carbon and one or more additional heteroatoms selected from O, N, or S;

$R_2$ is H, $C_{1-8}$ alkyl, $C_{1-3}$ alkyl-Ar, $C_{1-3}$ alkyl-$C_{3-6}$ cycloalkyl, $C_{2-8}$ alkenyl, $C_{2-4}$ alkenyl-Ar, or $C_{2-4}$ alkenyl-$C_{3-6}$ cycloalkyl;

Ar is substituted or unsubstituted phenyl;

$R_3$ is $NO_2$, halo, CN, C(O)$OR_7$, $COR_1$, or $NR_aR_b$ where $R_a$ and $R_b$ are independently H or $C_{1-6}$ alkyl;

$R_4$ is H, —$OC_{1-6}$ alkyl, halo, C(O)$NR_aR_b$, C(O)$OR_7$, $C_{1-8}$ alkyl, —$OCHF_2$, —$CH_2$ $OR_8$, —$OC_{1-3}$ alkylAr, or $CH_2NHC(O)CH_3$;

$R_5$ is H, halo, or alkyl;

$R_6$ is $C_{1-8}$ alkyl, $OC_{1-4}$ alkyl or halo;

$R_7$ is hydrogen or an ester or amide-forming group;

$R_8$ is hydrogen or $C_{1-6}$ alkyl;

or a pharmaceutically acceptable salt or solvate thereof.

Included in this invention are the novel compounds of Formula 1 and pharmaceutically acceptable formulations thereof.

DETAILED DESCRIPTION

These PDE7 inhibitors are useful in the treatment of a variety of allergic and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, ulcerative colitis, Crohn's disease, and chronic glomerulonephritis.

As regards preferred embodiments of the compounds disclosed herein, the following groups are preferred:

"Halo" means fluoro, chloro, bromo or iodo. The preferred halo groups are chloro and bromo.

"Alkenyl" refers to an unsaturated straight or branched hydrocarbon chain, which has 1 or more double bonds. Preferred groups are substituted ethenyl.

In $R_1$, Ra or $R_b$ is preferably hydrogen or lower alkyl, or $NR_aR_b$ is a 5-or 6-membered ring with or without a heteroatom. When Ra or $R_b$ is an alkyl group it is preferred that it be methyl or ethyl. Where $R_1$ is $NR_aR_b$ is a ring, the ring may be, for example: 1-imidazolyl, 2-R($_7$)-1-imidazolyl, 1-pyrazolyl, 3-(R$_7$)-pyrazolyl, 1-triazolyl, 2-triazolyl, 5-(R$_7$)-1-triazolyl, 5-(R$_7$)-2-triazolyl, 5-(R$_7$)-1-tetrazolyl, 5-(R$_7$)-2-tetrazolyl, 1-tetrazolyl, 2-tetrazolyl, morpholinyl, piperazinyl, 4-(R$_7$)-1-piperazinyl, pyrrolidinyl or pyrrolyl where $R_7$ is hydrogen or $C_{1-4}$ alkyl. The most preferred rings are morpholinyl and pyrrolidinyl.

Preferred $R_2$ groups are hydrogen, $C_{1-8}$ alkyl or $C_{1-3}$ alkyl-Ar where Ar is phenyl unsubstituted or substituted by C(O)$OR_7$.

Preferred $R_3$ groups are $NO_2$, Cl, Br, or $NR_aR_b$ where $R_a$ and $R_b$ are independently H or $C_{1-6}$ alkyl.

$R_4$ is preferably hydrogen, —$OC_{1-6}$ alkyl, Cl, C(O)$NR_aR_b$, $C_{1-4}$ alkyl, —$OCHF_2$, —$CH_2OR_8$, or —$OC_{1-3}$ alkylAr where Ar is phenyl, unsubstituted or substituted by C(O)$OR_7$.

$R_5$ is preferably hydrogen.

$R_6$ is preferably Cl, Br or methyl.

Compounds disclosed herein include the following:
2-methyl-5-nitro(N,N-dimethyl)benzenesulfonamide;
2-methyl-5-nitropyrrolidinylbenzenesulfonamide;
2-methyl-5-nitromorpholinobenzenesulfonamide;
2,4-dimethyl-5-nitro(N,N-dimethyl)benzenesulfonamide;
2-ethyl-5-nitro(N,N-dimethyl)benzenesulfonamide;
4-methoxy-2-methyl-5-nitro(N,N-dimethyl) benzenesulfonamide;
4-(3-carboxybenzyloxy)-2-methyl-5-nitro(N,N-dimethyl) benzenesulfonamide;

4-difluoromethoxy-2-methyl-5-nitro(N,N-dimethyl)
benzenesulfonamide;
4-bromo-2-methyl-5-nitro(N,N-dimethyl)
benzenesulfonamide;
4-amido-2-methyl-5-nitro(N,N-dimethyl)
benzenesulfonamide;
4-methyleneoxy-2-methyl-5-nitro(N,N-dimethyl)
benzenesulfonamide;
2-methyl-4-(methyl)methyleneoxy-5-nitro(N,N-dimethyl)benzenesulfonamide;
5-chloro-2-methyl(N,N-dimethyl)benzenesulfonamide;
2,5-dichloro-4-methyl(morpholino)benzenesulfonamide;
4,5-dichloro-2-methyl(N,N-dimethyl)
benzenesulfonamide;
2,4,5-trichloro(N,N-dimethyl) benzenesulfonamide;
2,5-dichloro-4-methoxy(N, N-dimethyl)
benzenesulfonamide;
2,5-dichloro-4-difluoromethoxy(N,N-dimethyl)
benzenesulfonamide;
5-bromo-2-methyl(N,N-dimethyl) benzenesulfonamide;
2-bromo-5-cyano(N,N-dimethyl)benzenesulfonamide;
3-N,N-dimethylamino-2-methyl(N,N-dimethyl)
benzenesulfonamide;
methyl 2,5-dichloro-4-(N-morpholino)sulfonyl benzoate;
2,5-dichloro-4-methyleneoxy(morpholino)
benzenesulfonamide;
2,5-dichloro-4-(methyl) methyleneoxy(morpholino)
benzenesulfonamide;
3,6-dichloro-2-methyl-4-methyleneoxy(morpholino)
benzenesulfonamide;
3,6-dichloro-2-(3-methoxy)phenethyl-4-methyleneoxy
(morpholino)benzenesulfonamide; or
N-(2,5-dichloro-4-morpholinosulfonyl)benzyl acetamide.

Formulations and Methods of Administration

The present compounds and pharmaceutically acceptable salts may be administered in a standard manner for the treatment of the indicated diseases, for example orally, parenterally, sub-lingually, dermally, transdermally, rectally, via inhalation or via buccal administration. A controlled-release preparation can also be utilized. An orally administered preparation is preferred.

The present compounds and pharmaceutically acceptable salts, which are active when given orally, can be formulated as syrups, tablets, capsules, controlled release preparation, or lozenges. A syrup formulation will generally consist of a suspension or solution of the compound or salt in a liquid carrier for example, ethanol, and peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises the present compound or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.3 mg to 60 mg/Kg, and preferably from 1 mg to 30 mg/Kg of a compound or a pharmaceutically acceptable salt thereof. Preferred doses include 10 mg and 15 mg/Kg. Each dosage unit for parenteral administration contains suitably from 0.1 mg to 100 mg/Kg, of the compound or a pharmaceutically acceptable salt thereof. Each dosage unit for intranasal administration contains suitably 1–400 mg and preferably 10 to 200 mg per person. A topical formulation contains suitably 0.01 to 5.0% of a present compound.

The active ingredient may be administered from 1 to 6 times a day, sufficient to exhibit the desired activity. Preferably, the active ingredient is administered about once or twice a day, more preferably once a day.

Methods of Preparation

Compounds of the Formula 1 wherein $R_1$ is exemplified by $N(CH_3)_2$ is H, $R_3$ is $NO_2$, $R_4$ is OH, $OCH_3$, $OCF_2H$; $R_5$ is H, and $R_6$ is $CH_3$ may be prepared by methods analogous to those described in Scheme 1.

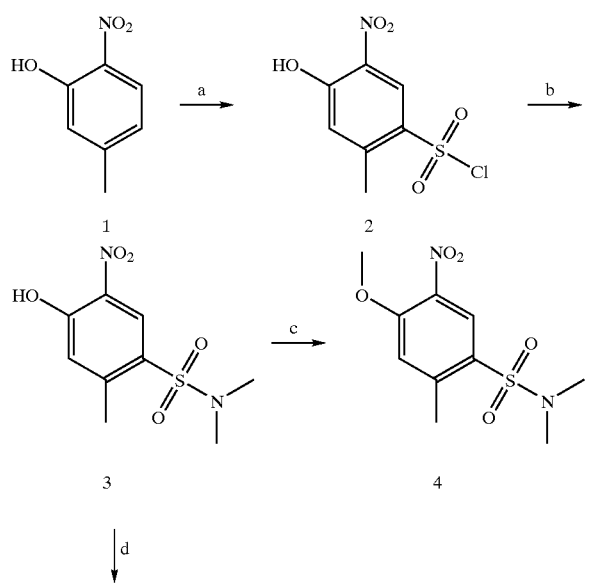

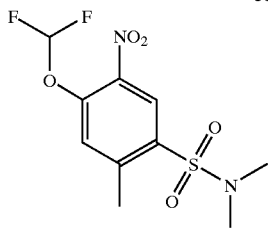

5

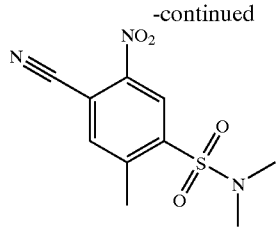

3

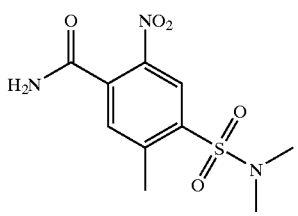

4

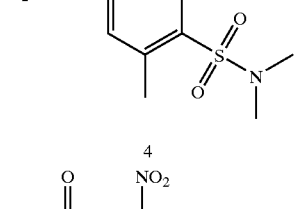

5

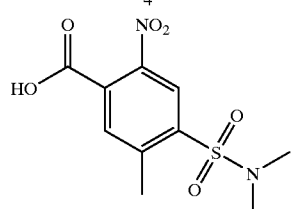

6

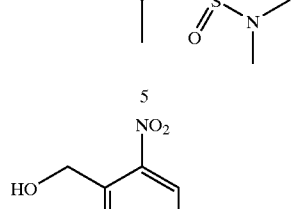

7

Arylsulfonyl chlorides, such as 2-Scheme-1, may be prepared from 5-methyl-2nitrophenol (available from Aldrich Chemical Co.) by conventional means such as treatment with chlorosulfonic acid. 2-Scheme-1 can be aminated by treatment with an excess of amine (such as dimethylamine) in a solvent such as methanol. Aryl ethers such as 4-Scheme-1 can be prepared by heating the phenol 3-Scheme-1 with a base such as cesium carbonate and the desired alkylating agent (such as dimethylsulfate) in an aprotic solvent such as DMF. The difluoromethyl ether 5-Scheme-1 can be prepared by refluxing phenol 3-Scheme-1 with sodium hydroxide and chlorodifluoroacetic acid in dimethylformamide.

Compounds of the formula 1 wherein $R_1$ is $NR_aR_b$ (where $R_aR_b$ is H or alkyl), or —$NR_aR_b$ together with the nitrogen form a 5 to 7 member ring comprised of carbon or carbon and one or more additional heteroatoms selected from O, N, or S; $R_2$ is H; $R_3$ is $NO_2$, Cl, Br, CN, COOH; $R_4$ is H, OH, halo, $C_{1-8}$ alkyl; $R_5$ is H, halo, or alkyl; $R_6$ is $C_{1-8}$ alkyl, an ether, or halo are prepared in an analogous manner to 3-Scheme-1, except substituting the appropriate aryl starting material.

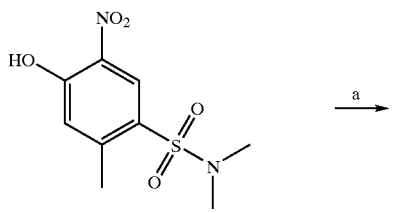

1

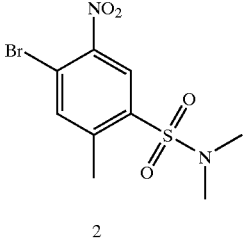

2

Conversion of the phenol into a carbon-based functionality can be accomplished by treating phenol 1-Scheme-2 with trifluoromethanesulfonic anhydride and triethylamine in dry methylene chloride. The resulting triflate can then be treated with tetrabutylammonium bromide in refluxing toluene to provide the halo-sulfonamide 2-Scheme-2. Formation of the amido-sulfonamide 4-Scheme-2 is accomplished by heating the halo sulfonamide 2-Scheme-2 with CuCN under argon in dry dimethylformamide, followed by hydrolysis of the resulting nitrile compound with a basic aqueous hydrogen peroxide solution. Preparation of the benzyl alcohol 6-Scheme-2 results from hydrolysis of the amido-sulfonamide to the carboxylate, followed by standard $BH_3$ in THF reduction conditions. The methyl ether 7-Scheme-2 is obtained by treatment of alcohol 6-Scheme-2 with dimethyl sulfate in methylene Chloride and 1 N NaOH under phase-transfer conditions using benzyltriethylammonium chloride as the phase transfer agent.

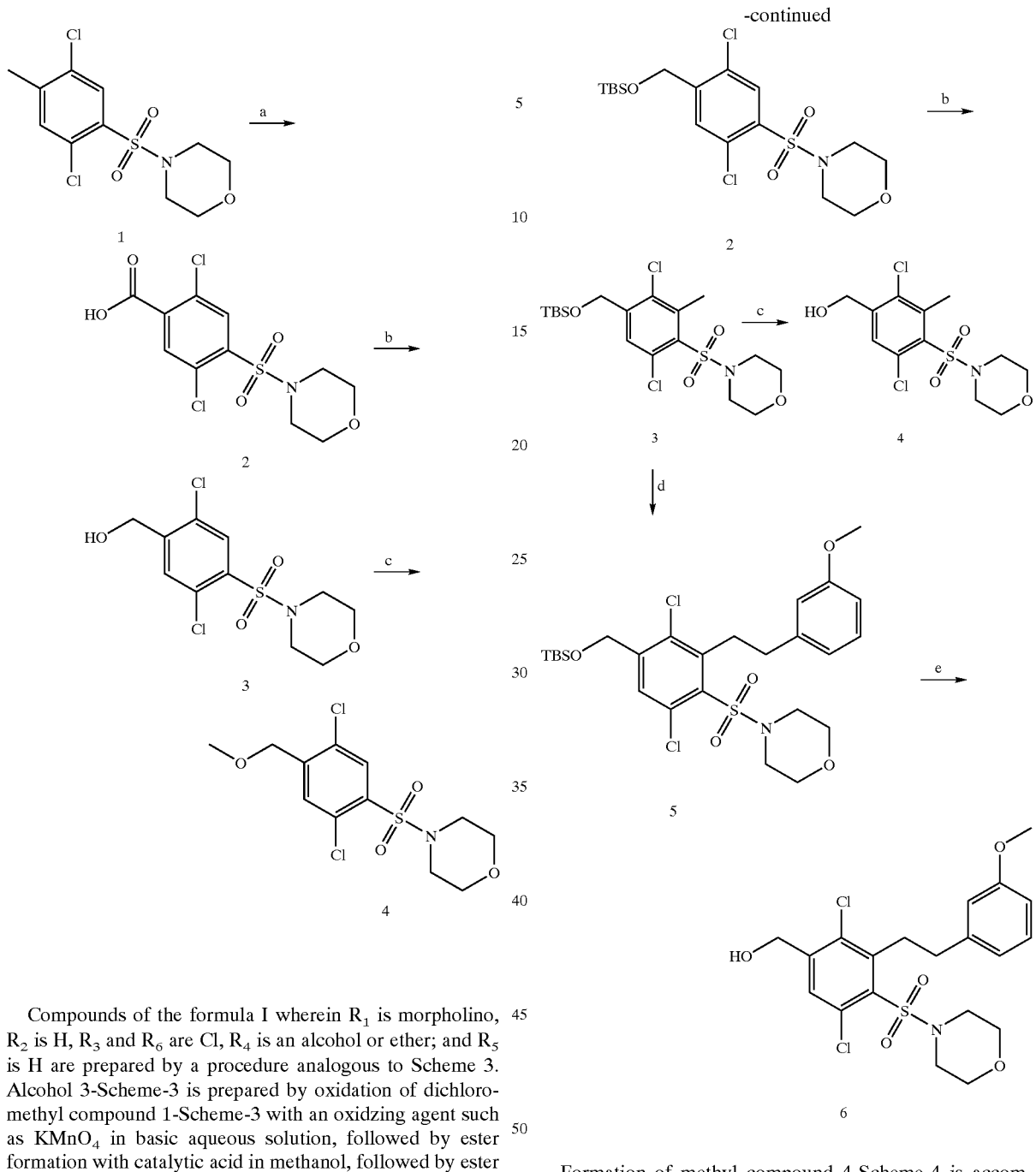

Compounds of the formula I wherein R₁ is morpholino, R₂ is H, R₃ and R₆ are Cl, R₄ is an alcohol or ether; and R₅ is H are prepared by a procedure analogous to Scheme 3. Alcohol 3-Scheme-3 is prepared by oxidation of dichloromethyl compound 1-Scheme-3 with an oxidzing agent such as KMnO₄ in basic aqueous solution, followed by ester formation with catalytic acid in methanol, followed by ester reduction with a suitable reducing agent such as Dibal to provide the alcohol. Formation of methyl ether 4-Scheme-3 is performed in a manner analogous to 7-Scheme-2.

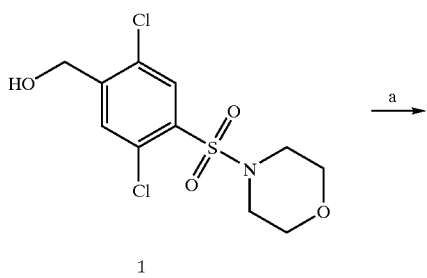

Formation of methyl compound 4-Scheme-4 is accomplished by protecting alcohol 1-Scheme-4 (3-Scheme-3) with the likes of a silyl protecting group (such as tert-butyldimethylsilyl) using standard procedures well known in the art. Deprotonation of the ortho-position to the sulfonamide with a strong base such as n-butyllithium in an aprotic solvent under anhydrous conditions, followed by addition of methyl iodide provides the protected methyl-compound 3-Scheme-4. Removal of the silyl group by treatment with tetrabutylammonium fluoride (TBAF) in tetrahydrofuran (THF) provides the alcohol 4-Scheme-4. Likewise, formation of the phenethyl compound 6-Scheme-4 can be accomplished in a similar manner by deprotonation of the methyl group of protected sulfonamide 3-Scheme-4 with a strong base under anhydrous conditions, followed by addition of 3-methoxybenzyl chloride. Deprotection of the alcohol with TBAF in THF provides the phenethyl-substituted benzenesulfonamide 6-Scheme-4.

Compounds of the Formula 1 wherein $R_4$ is exemplified by $CH_2NHC(O)CH_3$ are prepared by methods analogous to those described in Scheme 5.

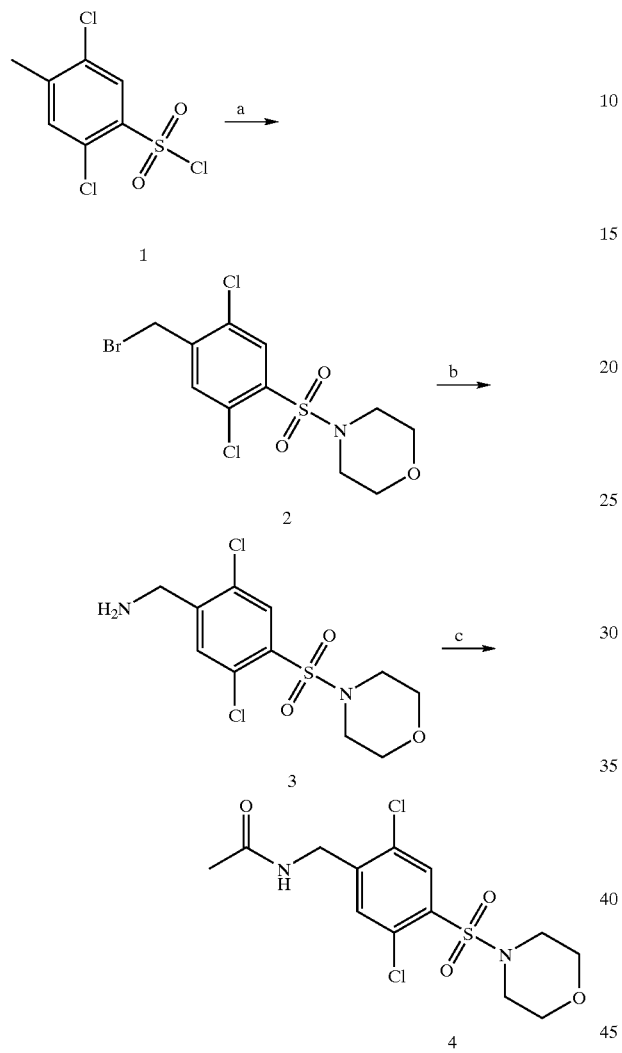

Bromination of sulfonyl chloride 1-Scheme-5 with n-bromosuccinamide (NBS), followed by treatment with morpholine provides benzyl bromide, 2-Scheme-5. Reaction of this bromide with ammonium hydroxide results in amine 3-Scheme-5. Amides such as 4-Scheme-5 may be prepared by conventional procedures for amide formation, such as treatment with an acid chloride (such as acetyl chloride) or using standard coupling procedures with a carboxylic acid (such as EDC and acetic acid).

The following examples are given to illustrate, but not limit, the invention described and claimed herein.

No deleterious or untoward effects are expected to occur when this invention is used in accordance with the teachings set forth herein.

SPECIFIC EXAMPLES

Example 1

2-Methyl-5-nitro(N,N-dimethyl)benzenesulfonamide

To a solution of 2-methyl-5-nitrobenzenesulfonyl chloride (5.0 g, 21.2 mmol) in 100 mL of methanol at 0° C. was added dimethylamine (5.3 mL of a 40% aqueous solution). The resulting reaction mixture was stirred at 0° C. for 10 min, during which time the product crashed out as white needles. The mixture was diluted with water and filtered, washing once with water. The needles were collected and dried in vacuo to provide 2-methyl-5-nitro(N,N-dimethyl) benzenesulfonamide (4.4 g, 85%), mp 72–74° C.

Proceeding in a similar manner, but substituting appropriate intermediates for those described above, the following compound was made:

2-Methyl-5-nitro-pyrrolidinylbenzenesulfonamide, white solid. Mass spectrum ES+: 316.4 (M+HCOOH). $^1$H NMR (400 MHz, CDCl$_3$): δ 1.97 (t, 4, J=6.7),2.75 (s, 3), 3.39 (t, 4, J=6.7), 7.51 (d, 1, J=8.4), 8.27 (dd, 1, J=8.4, 2.4), 8.69 (d, 1, J=2.4).

Example 2

2,4-Dimethyl-5-nitro(N,N-dimethyl) benzenesulfonamide

In a dry flask under argon filled with 2,4-dimethyinitrobenzene (1.0 g, 6.61 mmol), chlorosulfonic acid (5 mL) was added dropwise. The resulting solution was stirred at 130° C. for 4 h, and then the mixture was poured slowly onto ice. A light brown precipitate formed and was isolated by filtration. The solid was dissolved in methanol (20 mL), and dimethylamine (3 mL) was added with stirring. After 15 min, the reaction mixture was diluted with methylene chloride and 1 M HCl. The layers were separated, and the organics were dried and concentrated. Purification of the residue by flash chromatography (15% ethyl acetate/hexanes) provided 2,4-dimethyl-5-nitro (N,N-dimethyl) benzenesulfonamide (626 mg, 37%) as a white solid. Anal. Calcd for $C_{10}H_{14}N_2O_4S$: C, 46.50; H, 5.46; N, 10.85. Found: C, 46.68; H, 5.25; N, 10.71.

Proceeding in a similar manner, but substituting appropriate intermediates for those described above, the following compound was made:2-Ethyl-5-nitro(N,N-dimethyl) benzenesulfonamide, white solid, mp 113° C. Anal. Calcd for $C_{10}H_{14}N_2O_4S$: C, 46.50; H, 5.46; N, 10.85. Found: C, 46.56; H, 5.35; N, 10.77.

Example 3

4-Methoxy-2-methyl-5-nitro(N,N-dimethyl) benzenesulfonamide 3a. 4-Hydroxy-2-methyl-5-nitro(N,N-dimethyl) benzenesulfonamide A dry flask under argon was charged with chlorosulfonic acid (25 mL) and chloroform (15mL). The resulting solution was cooled to 0° C., and 5-methyl-2-nitrophenol (10 g) was added as a chloroform solution (30 mL) dropwise with stirring. After stirring at 0° C. for 10 min, the dark reaction solution was heated to 60° C. and stirred for 1 h. Once the solution had returned to room temperature, it was poured slowly onto a large amount of ice (~500 g). The resulting mixture was extracted with methylene chloride, and excess dimethylamine (40% aqueous) was added to the organic extracts with stirring. This reaction mixture was stirred for 15 min, then quenched with 1 M HCl. The layers were separated, and the aqueous layer was extracted once with methylene chloride. The combined organics were dried and concentrated to provide 4-hydroxy-2-methyl-5-nitro(N, N-dimethyl) benzenesulfonamide (12.93 g, 76%) as a yellow solid. Mass spectrum ES-: 259.1 (M-H).

3b. 4-Methoxy-2-methyl-5-nitro(N,N-dimethyl) benzenesulfonamide

To a solution of 4-hydroxy-2-methyl-5-nitro(N,N-dimethyl)benzenesulfonamide (100 mg, 0.39 mmol) in dry DMF (1 mL) was added cesium carbonate (125 mg, 0.39 mmol) and dimethylsulfate (50 mg, 0.39 mmol). The resulting reaction mixture was heated to 60° C. and stirred for 3 h. After cooling to room temperature, the reaction was diluted with ethyl acetate and 1 N NaOH. The layers were separated, and the organics were washed once with 1 N NaOH. The organics were then dried and concentrated to provide 4-methoxy-2-methyl-5-nitro(N,N-dimethyl) benzenesulfonamide (90 mg, 85%) as a yellow solid, mp 130–132° C. Mass spectrum ES+: 275.0 (M+H).

Proceeding in a similar manner, but substituting appropriate intermediates for those described above, the following compound was made:

4-(3-Methylbenzoate)methyleneoxy-2-methyl-5-nitro(N,N-dimethyl)-benzenesulfonamide pale yellow solid, mp 138–139° C. Mass spectrum ES+: 454.3 (M+HCOOH).

Example 4

4-(3-Carboxybenzyloxy)-2-methyl-5-nitro(N,N-dimethyl) benzenesulfonamide

To a solution of 4-(3-methylbenzoate)methyleneoxy-2-methyl-5-nitro(N,N-dimethyl) benzenesulfonamide (80 mg) in dioxane (7 mL) was added 1 N KOH (3 mL). The reaction mixture was stirred for 2 h, then quenched with 1 M HCl and diluted with ethyl acetate. The layers were separated, and the organics were dried and concentrated to provide 4-(3-carboxybenzyloxy)-2-methyl-5-nitro(N,N-dimethyl) benzenesulfonamide (76 mg, 100%) as a white solid, mp 220–221° C. Anal. Calcd for $C_{17}H_{18}N_2O_7S$: C, 47.54; H, 3.74; N, 3.46. Found: C, 47.62; H, 3.77; N, 3.32.

Example 5

4-Difluoromethoxy-2-methyl-5-nitro(N,N-dimethyl) benzenesulfonamide

To a solution of 4-hydroxy-2-methyl-5-nitro(N,N-dimethyl)benzenesulfonamide (200 mg, 0.77 mmol) in dry DMF (2 mL) was added sodium hydroxide (74 mg, 1.85 mmol) and chlorodifluoroacetic acid (120 mg, 0.92 mmol). The resulting reaction mixture was stirred at 120° C. for 18 h. After cooling, the reaction was diluted with water and ethyl acetate, and the layers were separated. The organics were washed three times with 1 N NaOH, dried and concentrated. The residue was purified by flash chromatography (20% ethyl acetate/hexanes) to provide 4-difluoromethoxy-2-methyl-5-nitro (N,N-dimethyl)-benzenesulfonamide (51 mg, 21%) as a yellow solid, mp 125–126° C.

Example 6

4-Bromo-2-methyl-5-nitro(N,N-dimethyl) benzenesulfonamide

6a. 4-Trifluoromethanesulfonyloxy-2-methyl-5-nitro (N,N-dimethyl)-benzenesulfonamide To a solution of 4-hydroxy-2-methyl-5-nitro(N,N-dimethyl) benzenesulfonamide (55 mg, 0.21 mmol) in methylene chloride (2 mL) under argon was added triethylamine (25 mg, 0.24 mmol) followed by trifluoromethanesulfonic anhydride (69 mg, 0.24 mmol). The reaction solution was stirred for 5 min, then quenched with water and diluted with methylene chloride. The layers were separated, and the organics were dried and concentrated to provide 4-trifluoromethanesulfonyloxy-2-methyl-5-nitro (N,N-dimethyl) benzenesulfonamide (78 mg, 94%) as a yellow oil that crystallized upon standing.

6b. 4-Bromo-2-methyl-5-nitro(N,N-dimethyl) benzenesulfonamide

To a solution of 4-trifluoromethanesulfonyloxy-2-methyl-5-nitro(N,N-dimethyl) benzenesulfonamide (55 mg, 0.14 mmol) in dry toluene was added tetrabutylammonium bromide (90 mg, 0.28 mmol). The resulting mixture was stirred at a reflux for 4 h. After cooling, the reaction was diluted with ethyl acetate and water, and the layers were separated. The organics were dried and concentrated, and the residue was purified by flash chromatography (30% ethyl acetate/hexanes) to provide 4-bromo-2-methyl-5-nitro(N,N-dimethyl)benzenesulfonamide (43 mg, 95%) as a white solid. $^1$H NMR (400 MHz, $CDCl_3$): δ 2.67 (s, 3), 2.88 (s, 6), 7.74 (s, 1), 8.37 (s, 1).

Example 7

4-Amido-2-methyl-5-nitro(N,N-dimethyl) benzenesulfonamide

7a. 4-Cyano-2-methyl-5-nitro(N,N-dimethyl) benzenesulfonamide

To a solution of 4-bromo-2-methyl-5-nitro(N,N-dimethyl)benzenesulfonamide (450 mg, 1.42 mmol) in dry DMF (14 mL) under argon was added CuCN (178 mg, 1.99 mmol). The resulting mixture was heated to 115° C. and stirred for 4 h. The reaction was cooled and diluted with water and ethyl acetate. The layers were separated, and the organics were washed once with water. The organics were then dried, concentrated, and purified by flash chromatography (35% ethyl acetate/hexanes) to provide 4-cyano-2-methyl-5-nitro-(N,N-dimethyl)benzenesulfonamide (249 mg, 65%) as pale yellow crystals. IR (thin film): 2240 $cm^{-1}$. $^1$H NMR (400 MHz, $CDCl_3$): δ2.78 (s, 3), 2.94 (s, 6), 7.87 (s, 1), 8.74 (s, 1).

7b. 4-Amido-2-methyl-5-nitro(N,N-dimethyl) benzenesulfonamide

A suspension of 4-cyano-2-methyl-5-nitro(N,N-dimethyl) benzenesulfonamide (230 mg, 0.86 mmol) in ethanol (8 mL) was heated at 90° C. to dissolve all the solid. Once the solution was homogeneous, 30% aqueous hydrogen peroxide (2.25 mL) was added, followed by 1 N NaOH (2.25 mL). After stirring for 10 min at 90° C., the reaction was cooled to room temperature and quenched with 1 M HCl. The solution was extracted twice with methylene chloride, and the organics were dried and concentrated to provide 4-amido-2-methyl-5-nitro(N,N-dimethyl) benzenesulfonamide (221 mg, 90%) as a yellow solid. Mass spectrum ES+: 288.2 (M+H). $^1$H NMR (400 MHz, $d_6$—DMSO): δ 2.66 (s, 3), 2.81 (s, 6), 7.75 (s, 1), 7.88 (br s, 1), 8.20 (br s, 1), 8.30 (s, 1).

Example 8

4-Methyleneoxy-2-methyl-5-nitro(N,N-dimethyl) benzenesulfonamide

8a. 4-Carboxy-2-methyl-5-nitro(N,N-dimethyl) benzenesulfonamide

To a stirring solution of 4-amido-2-methyl-5-nitro(N,N-dimethyl) benzenesulfonamide (16 mg, 0.056 mmol) in water (1 mL) and $H_2SO_4$ (0.5 mL) at 0° C. was added $NaNO_2$ (20 mg) as a 0.3 mL aqueous solution, which was added slowly via pipet below the reaction solution surface. The resulting mixture was then heated to 50° C. and stirred for 10 min. The reaction was cooled and diluted with methylene chloride and water. The layers were separated, and the organics were dried and concentrated to provide 4-carboxy-2-methyl-5-nitro(N,N-dimethyl) benzenesulfonamide (16 mg, 100%) as an off-white solid. $^1$H NMR (400 MHz, $d_4$—MeOH): δ 2.72 (s, 3), 2.85 (s, 6), 7.81 (s, 1), 8.35 (s, 1).

8b. 4-Methyleneoxy-2-methyl-5-nitro(N,N-dimethyl)benzenesulfonamide

To a solution of 4-carboxy-2-methyl-5-nitro(N,N-dimethyl)benzenesulfonamide (50 mg, 0.17 mmol) in dry THF (3 mL) under argon was added $BH_3$ in THF (0.55 mL, 0.55 mmol). The reaction solution was heated to a reflux and stirred for 3 h. After cooling, the reaction was quenched by the slow addition of 1 M HCl (3 ml), and the resulting mixture was stirred at 60° C. for 1 h. After this time, the mixture was diluted with ethyl acetate and water, and the organics were separated, dried, and concentrated. Purification of the residue by flash chromatography (35% ethyl acetate/hexanes) provided 4-methyleneoxy-2-methyl-5-nitro(N,N-dimethyl) benzenesulfonamide (41 mg, 86%) as pale yellow crystals. Mass spectrum ES–: 273.2 (M–H).

Example 9

2-Methyl-4-(methyl)methyleneoxy-5-nitro(N,N-dimethyl) benzenesulfonamide

To a solution of 4-methyleneoxy-2-methyl-5-nitro(N,N-dimethyl)-benzenesulfonamide (90 mg, 0.33 mmol) in methylene chloride (3 mL) was added 1 N NaOH (3 mL), dimethyl sulfate (124 mg, 0.99 mmol), and benzyltriethylammonium chloride (7 mg). The resulting biphasic mixture was stirred at room temperature for several hours until all the starting alcohol had been consumed (monitored by TLC). Then the layers were separated, and the organics were dried and concentrated. Purification of the residue by preparative HPLC provided 2-methyl-4-(methyl) methyleneoxy-5-nitro (N,N-dimethyl)benzenesulfonamide (25 mg, 26%) as yellow crystals. Anal. Calcd for $C_{11}H_{16}N_2O_5S$: C, 45.82; H, 5.59; N, 9.72. Found: C, 45.81; H, 5.40; N, 9.43.

Example 10

5-Chloro-2-methyl(N,N-dimethyl) benzenesulfonamide

To a solution of p-chlorotoluene (1.0 g, 7.90 mmol) in chloroform (5 mL) under argon at 0° C. was added chlorosulfonic acid (4 mL) dropwise. The resulting solution was heated to 50° C. and stirred for 15 min. Once the solution had returned to room temperature, it was poured slowly onto ice. The resulting mixture was extracted with methylene chloride, and the organics were dried and concentrated. The residue was dissolved in methanol (20 mL), and excess dimethylamine (2 mL of a 40% aq. solution) was added with stirring. This reaction mixture was stirred for 15 min, then quenched with 1 M HCl. The layers were separated, and the combined organics were dried and concentrated. Purification of the residue by flash chromatography provided 5-chloro-2-methyl (N,N-dimethyl)benzenesulfonamide (1.34 g, 73%) as a colorless oil. Mass spectrum ES+: 279.1 (M+HCOOH). Anal. Calcd for $C_9H_{12}ClNO_2S$: C, 46.25; H, 5.18; N, 5.99. Found: C, 46.31; H, 4.88; N, 5.56.

Proceeding in a similar manner, but substituting appropriate intermediates for those described above, the following compounds were made:

2,5-Dichloro-4-methyl(morpholino)benzenesulfonamide, white solid. Anal. Calcd for $C_{11}H_{13}Cl_2NO_3S$: C, 42.59; H, 4.22; N, 4.52. Found: C, 42.91; H, 4.17; N, 4.53.

4,5-Dichloro-2-methyl(N,N-dimethyl) benzenesulfonamide, white solid, mp 109° C. $^1$H NMR (400 MHz, $CDCl_3$): δ 2.56 (s, 3), 2.82 (s, 6), 7.42 (s, 1), 7.96 (s, 1).

5-Bromo-2-methyl(N,N-dimethyl)benzenesulfonamide, white solid, mp 99–100° C. Mass spectrum ES+: 280.1 (M+2).

2-Bromo-5-carboxy(N,N-dimethyl)benzenesulfonamide, white solid, mp 249–251° C.

Example 11

2-Bromo-5-cyano(N,N-dimethyl) benzenesulfonamide

11a. Methyl 4-bromo-3-(N,N-dimethyl) benzenesulfamidobenzoate

A solution of 2-bromo-5-carboxy(N,N-dimethyl) benzenesulfonamide (1.32 g, 4.29 mmol) and concentrated $H_2SO_4$ (0.3 mL) in methanol (20 mL) was stirred at a reflux for 5.5 h. After this time, the reaction solution was cooled and concentrated. Purification of the residue by flash chromatography (30% ethyl acetate/hexanes) provided methyl 4-bromo-3-(N,N-dimethyl)benzenesulfamidobenzoate (970 mg, 70%) as a white solid, mp 103–104° C.

11b. 2-Bromo-5-methyleneoxy(N,N-dimethyl) benzenesulfonamide

To a solution of methyl 4-bromo-3-(N,N-dimethyl) benzenesulfamidobenzoate (100 mg, 0.31 mmol) in dry toluene (3 mL) at 78° C. was added diisobutylaluminum hydride in hexanes (0.77 mL, 0.77 mmol). The reaction solution was warmed to room temperature and stirred for 10 min, then recooled to 78° C. and quenched with methanol. After warming to room temperature, the reaction was diluted with ethyl acetate and washed with 0.5M HCl. The organics were dried and concentrated to provide 2-bromo-5-methyleneoxy(N,N-dimethyl)benzenesulfonamide (86 mg, 94%) as a thick colorless oil.

11c. 4-Bromo-3-(N,N-dimethyl) benzenesulfamidobenzaldehyde

To a solution of 2-bromo-5-methyleneoxy(N,N-dimethyl) benzenesulfonamide (86 mg, 0.29 mmol) in methylene chloride (4 mL) at 0° C. was added PDC (220 mg, 0.59 mmol). The resulting suspension was stirred at room temperature for 2.5 h. After this time the reaction was diluted with water and ethyl acetate, and the layers were separated. The organics were dried and concentrated to provide 4-bromo-3-(N,N-dimethyl) benzenesulfamidobenzaldehyde (64 mg, 76%) as a pale yellow oil that crystallized upon standing.

11d. 2-Bromo-5-cyano(N,N-dimethyl) benzenesulfonamide

A solution of 4-bromo-3-(N,N-dimethyl) benzenesulfamidobenzaldehyde (64 mg, 0.22 mmol) and $H_2NOH$ HCl (20 mg, 0.28 mmol) in formic acid (1.5 mL) was stirred at a reflux under argon for 2.5 h. Then the reaction was diluted with ice and brought to neutral pH with 1 N NaOH. The mixture was extracted with ethyl acetate, and the organics were dried and concentrated. Purification of the residue by preparative HPLC provided 2-bromo-5-cyano-(N,N-dimethyl)benzenesulfonamide (22 mg, 35%) as a white solid. $^1$H NMR (400 MHz, CDCl$_3$): δ 2.94 (s, 6), 7.64 (dd, 1,J=8.1, 2.0), 7.89 (d, 1, J=8.1), 8.36 (d, 1, J=2.0).

Example 12

3-N,N-Dimethylamino-2-methyl(N,N-dimethyl) benzenesulfonamide 12a. 3-Amino-2-methyl(N,N-dimethyl) benzenesulfonamide A suspension of 2-methyl-5-nitro(N,N-dimethyl) benzenesulfonamide (2.0 g, 8.20 mmol) and Pd/C (0.30 g) in ethanol (40 mL) was stirred under an H$_2$ balloon for 16 h. The suspension was filtered through Celite and washed with methylene chloride. The filtrate was concentrated to provide 3-amino-2-methyl(N,N-dimethyl) benzenesulfonamide (1.72 g, 98%) as a white solid.

12b. 3-N,N-Dimethylamino-2-methyl(N,N-dimethyl)benzenesulfonamide

To a stirring solution of 3-amino-2-methyl(N,N-dimethyl) benzenesulfonamide (330 mg, 1.54 mmol) in methylene chloride (5 mL) under argon was added 37% aq. formaldehyde (0.12 mL, 1.54 mmol), followed by sodium triacetoxyborohydride (458 mg, 2.16 mmol) and acetic acid (93 mg, 1.54 mmol). The resulting solution was stirred for 1 h, and then the reaction diluted with 1 N NaOH and methylene chloride. The layers were separated, and the organics were dried and concentrated. Purification of the residue by flash chromatography (30% ethyl acetate/hexanes) provided 3-N,N-dimethylamino-2-methyl-(N,N-dimethyl)benzenesulfonamide (68 mg, 18%) as a white solid, mp 123° C. Mass spectrum ES+: 243.4 (M+H).

Example 13

4-Carboxy-2,5-dichloro(morpholino) benzenesulfonamide

To a solution of 2,5-dichloro-4-methyl(morpholino) benzenesulfonamide (773 mg, 2.5 mmol) in pyridine (15 mL) and water (15 mL) at 70° C. was added KMnO$_4$ (1.2 g, 7.50 mmol). The resulting mixture was stirred for 1 h, and then another 500 mg of KMnO$_4$ was added. After stirring at 70° C. overnight, the reaction was filtered via Buchner funnel, washing the precipitated MnO2 with water. The filtrate was diluted with ~50 mL 1 N NaOH and extracted 4 times with ethyl acetate. The aqueous layer was then acidified with 1 M HCl and extracted twice with ethyl acetate. These second organic extracts were dried and concentrated to provide 4-carboxy-2,5-dichloro (morpholino) benzenesulfonamide (295 mg, 35%) as white crystals. Mass spectrum ES−: 339.8 (M−H).

Example 14

2,5-Dichloro-4-methyleneoxy(morpholino) benzenesulfonamide

A solution of 4-carboxy-2,5-dichloro(morpholino) benzenesulfonamide (1.85 g, 5.44 mmol) and concentrated H$_2$SO$_4$ (3 mL) in methanol (50 mL) was stirred at a reflux overnight. After cooling, the solution was diluted with methylene chloride and water, and the layers were separated. The organics were dried and concentrated to a white solid, which was dissolved in a mixture of dry toluene (25 mL) and dry methylene chloride (10 mL). This solution was cooled to 78° C., and diisobutylaluminum hydride in hexanes (14 mL, 14.0 mmol) was added dropwise. The resulting solution was stirred at 78° C. for 15 min, then warmed to room temperature and stirred for 10 min. After recooling to 78° C., the reaction was quenched by the slow addition of 1 M HCl. The mixture was extracted twice with ethyl acetate, and the combined organics were dried and concentrated. Purification of the residue by flash chromatography (30% ethyl acetate/hexanes) provided 2,5-dichloro-4-methyleneoxy (morpholino)benzenesulfonamide (1.25 g, 71%) as a white solid. Anal. Calcd for C$_{11}$H$_{13}$Cl$_2$NO$_4$S: C, 40.50; H, 4.02; N, 4.31. Found: C, 40.09; H, 3.93; N, 3.96.

Example 15

2,5-Dichloro-4-(methyl)methyleneoxy(morpholino) benzenesulfonamide

To a solution of 2,5-dichloro-4-methyleneoxy (morpholino)benzenesulfonamide (100 mg, 0.31 mmol) in methylene chloride (3 mL) was added 1 N NaOH (3 mL), dimethyl sulfate (116 mg, 0.92 mmol), and benzyltriethylammonium chloride (7 mg). The resulting biphasic solution was stirred for several hours until all the starting material was consumed (monitored by TLC). Then the reaction mixture was diluted with more methylene chloride and water, and the layers were separated. The organics were dried and concentrated. Purification of the residue by preparative HPLC provided 2,5-dichloro-4-(methyl)methyleneoxy(morpholino)benzenesulfonamide (30 mg, 29%) as white crystals. Anal. Calcd for C$_{12}$H$_{15}$Cl$_2$NO$_4$S: C, 42.36; H, 4.44; N, 4.12. Found: C, 42.30; H, 4.22; N, 3.92.

Example 16

3,6-Dichloro-2-methyl-4-methyleneoxy(morpholino) benzenesulfonamide 16a. 2,5-Dichloro-4-(methylene)tert-butyldimethylsilyloxy(morpholino)-benzenesulfonamide To a solution of 2,5S-dichloro-4-(methyl)methyleneoxy (morpholino)-benzenesulfonamide (250 mg, 0.77 mmol) in DMF (1 mL) under argon was added imidazole (209 mg, 3.0 mmol) and tert-butyidimethylsiloxy chloride (TBDMSCI) (232 mg, 1.5 mmol). After stirring for 5 min, the reaction was diluted with ethyl acetate and 0.5M HCl. The layers were separated, and the organics were dried and concentrated to provide 2,5-dichloro-4-(methylene)tert-butyidimethylsilyloxy(morpholino) benzenesulfon amide (340 mg, 100%) as a white solid.

16b. 3,6-Dichloro-2-methyl-4-(methylene)tert-butyldimethylsilyloxy-(morpholino) benzenesulfonamide To a solution of 2,5-dichloro-4-(methylene) tert-butyldimethylsilyloxy-(morpholino)benzenesulfonamide (93 mg, 0.21 mmol) in dry THF (2 mL) at 78° C. under argon was added n-butyllithium in hexanes (0.24 mL, 0.36 mmol). The solution was allowed to stir for 10 min, and then methyl iodide (90 mg, 0.64 mmol) was added. The ice bath was removed and the reaction warmed to room temperature, during which time the dark yellow color of the anion disappeared. After stirring at room temperature for 45 min, the reaction was quenched with 0.5M HCl and diluted with ethyl acetate. The organics were dried and concentrated to provide 3,6-dichloro-2-methyl-4-(methylene) tert-butyidimethyl-silyloxy(morpholino)benzenesulfonamide (88 mg, 92%) as a thick oil.

16c. 3,6-Dichloro-2-methyl-4-methyleneoxy (morpholino)benzenesulfonamide

To a solution of 3,6-dichloro-2-methyl-4-(methylene)tert-butyldimethylsilyloxy-(morpholino)benzenesulfonamide (88 mg, 0.19 mmol) in THF (2 mL) at 0° C. was added TBAF in THF (0.23 mL, 0.23 mmol). The reaction solution was stirred for 15 min, then diluted with water and ethyl acetate. The layers were separated, and the organics were dried and concentrated to provide 3,6-dichloro-2-methyl-4-methyleneoxy-(morpholino)benzenesulfonamide (10 mg, 15%) as a white solid. Mass spectrum ES+: 340.0.

Example 17

3,6-Dichloro-2-(3-methoxy)phenethyl-4-methyleneoxy(morpholino) benzenesulfonamide

17a. 3,6-Dichloro-2-(3-methoxy)phenethyl-4-(methylene)tert-butyl-dimethylsilyloxy (morpholino) benzenesulfonamide To a solution of 3,6-dichloro-2-methyl-4-(methylene)tert-butyldimethylsilyloxy-(morpholino)benzenesulfonamide (150 mg, 0.33 mmol) in dry THF (3 mL) under argon at 78° C. was added n-butyllithium in hexanes (0.34 mL, 0.50 mmol). The resulting bright red solution was allowed to stir at 78° C. for 10 min, and then 3-methoxybenzyl chloride (79 mg, 0.50 mmol) was added. The reaction solution was warmed slowly to room temperature and stirred for 1 h. After this time the reaction was quenched with water and diluted with ethyl acetate. The layers were separated, and the organics were dried and concentrated. Purification of the residue by flash chromatography (5% ethyl acetate/hexanes) provided 3,6-dichloro-2-(3-methoxy) phenethyl-4-(methylene)tert-butyidimethylsilyloxy-(morpholino) benzenesulfonamide (47 mg, 25%) as a colorless oil.

17b. 3,6-Dichloro-2-(3-methoxy)phenethyl-4-methyleneoxy(morpholino)-benzenesulfonamide To a solution of:3,6-dichloro-2-(3-methoxy)phenethyl-4-(methylene)tert-butyldimethylsilyloxy(morpholino) benzenesulfonamide (47 mg, 0.08 mmol) in THF (1 mL) at 0° C. was added TBAF in THF (0.1 mL, 0.1 mmol). The reaction solution was stirred for 15 min, then diluted with water and ethyl acetate. The layers were separated, and the organics were dried and concentrated to provide 3,6-dichloro-2-(3-methoxy)phenethyl-4-methyleneoxy (morpholino)benzenesulfonamide (4 mg, 11%) as a white gum. Mass spectrum ES+: 460.0.

Example 18

N-(2,5-Dichloro-4-morpholinosulfonyl)benzyl Acetamide

18a. 2,5-Dichloro-4-methyl-benzenesulfonyl Chloride

A dry flask under argon was charged with chlorosulfonic acid (30 mL) and cooled to 0° C. 2,5-Dichlorotoluene (10 g, 62.1 mmol) was then added dropwise, and once the addition was complete, the reaction was heated to 60° C. and stirred for 30 min. After cooling to room temperature, the reaction mixture was poured slowly onto ice. The aqueous mixture was extracted twice with methylene chloride, and the organics were dried and concentrated to provide 2,5-dichloro-4-methylbenzenesulfonyl chloride (14.14 g, 88%) as a white solid.

18b. N-(2,5-Dichloro-4-morpholinosulfonyl)benzyl bromide

To a stirring solution of 2,5-dichloro-4-methylbenzenesulfonyl chloride (14.14 g, 54.6 mmol) in refluxing $CCl_4$ (40 mL) under a sunlamp was added bromine (9.6 g, 60 mmol) as a $CCl_4$ solution over 30 min. The reaction was then allowed to stir at a reflux under the sunlamp for 3 h. After cooling to room temperature, potassium carbonate (16.6 g, 120 mmol) and morpholine (5.2 g, 60 mmol) were added. The resulting mixture was stirred for 3 h, then diluted with methylene chloride and water. The layers were separated, and the organics were dried and concentrated to provide N-(2,5-dichloro-4-morpholinosulfonyl)benzyl bromide (21.2 g, 99%) as a crude white solid.

18c. N-(2,5-Dichloro-4-morpholinosulfonyl)benzyl amine

To a rapidly stirring solution containing dioxane (100 mL) and aq. ammonia (300 mL), a solution of N-(2,5-dichloro-4-morpholinosulfonyl)benzyl bromide (21.2 g, 54 mmol) in dioxane (300 mL) was added in a slow stream. The resulting solution was stirred for 1 h, then diluted with ethyl acetate and brine. The layers were separated, and the aqueous layer was extracted with ethyl acetate. The combined organics were dried, concentrated, and chromatographed (100% ethyl acetate) to provide N-(2,5-dichloro-4-morpholinosulfonyl) benzyl amine (4.2 g, 21%) as a pale yellow solid.

18d. N-(2,5-Dichloro-4-morpholinosulfonyl)benzyl acetamide

To a stirring solution of N-(2,5-dichloro-4-morpholinosulfonyl)benzyl amine (85 mg, 0.26 mmol) in methylene chloride (5 mL was added triethylamine (32 mg, 0.31 mmol) and acetic anhydride (34 mg, 0.31 mmol). After stirring for 30 min, the reaction was quenched with 1 M HCl and extracted with methylene chloride. The organics were dried and concentrated. Purification of the residue by preparative HPLC provided N-(2,5-dichloro-4-morpholinosulfonyl)benzyl acetamide (40 mg, 42%) as a white solid. $^1$H NMR (400 MHz, $d_6$—DMSO): δ 1.94 (s, 3), 3.18 (t, 4, J=4.7), 3.60 (t, 4, J=4.7), 4.35 (d, 2, J=5.8), 7.58 (s, 1), 7.93 (s, 1), 8.50 (t, 1, J=5.8).

Measurement of Phosphodiesterase (PDE) Activity

Phosphodiesterase activity was assayed using a [$^3$H] cAMP SPA enzyme assay (Amersham Pharmacia Biotech code TRKQ 7090) as described by the supplier with minor modifications. The reactions were conducted in 96-well plates at room temperature in 100 ul reaction buffer containing (final concentrations): 50 mM Tris-HCl, pH 7.5, 8.3 mM $MgCl_2$, 1.7 mM EGTA 100 nM [$^3$H]cAMP (approximately 30000 DPM/pmol as determined in a Beckman LS-6500 scintillation counter), enzyme (human recombinant PDE7A1 [*Michaeli, T., et al, J. Bio. Chem 268(17), 12925–12932]) and inhibitors or vehicle. The enzyme concentration was adjusted so that approximately 20% or less of the substrate was hydrolyzed, keeping it within the linear range of activity. Appropriate concentrations of the inhibitors were used for determination of their $IC_{50}$ values. The assay was allowed to proceed for 60 minutes at room temperature and was terminated by the addition 50 ul of the SPA yttrium silicate bead suspension in the presence of zinc sulfate. The plates were then routinely shaken for 5 minutes on a-microtiter plate shaker after which the beads were allowed to settle for at least 20 minutes prior to measuring the radioactivity using a Packard Topcount microplate scintillation counter.

In the presence of zinc sulfate, the linear nucleotide product, 5'AMP, binds preferentially to the SPA yttrium silicate beads as compared to the cyclic nucleotide substrate, cAMP. The scintillant contained within the SPA beads is excited when the radiolabeled product binds to the beads whereas unbound substrate will not be in close enough proximity to generate a signal.

What is claimed is:

1. A method for inhibiting the enzymatic or catalytic activity of PDE7 in mammals which comprises administering to a mammal in need thereof an effective amount of a compound of Formula 1:

wherein, $R_1$ is $NR_aR_b$ where $R_a$ and $R_b$ are independently H or $C_{1-6}$ alkyl;

$R_2$ is H, $C_{1-8}$alkyl, $C_{1-3}$alkyl-Ar, $C_{1-3}$alkyl-$C_{3-6}$cycloalkyl, $C_{2-8}$alkenyl, $C_{2-4}$alkenyl-Ar, or $C_{2-4}$alkenyl-$C_{3-6}$cycloalkyl;

Ar is substituted or unsubstituted phenyl;

$R_3$ is $NO_2$, halo, CN, $C(O)OR_7$, $COR_1$, or $NR_aR_b$ where $R_a$ and $R_b$ are independently H or $C_{1-6}$alkyl;

$R_4$ is H, —$OC_{1-6}$alkyl, halo, $C(O)NR_aR_b$, $C(O)OR_7$, $C_{1-8}$alkyl, —$OCHF_2$, $CH_2OR_8$, —$OC_{1-3}$alkylAr or $CH_2NH(O)CH_3$;

$R_5$ is H, halo, or alkyl;

$R_6$ is $C_{1-8}$alkyl, $OC_{1-4}$alkyl or halo;

$R_7$ is hydrogen or an ester or amide-forming group;

$R_8$ is hydrogen or $C_{1-6}$alkyl;

or a pharmaceuticaly acceptable salt or solvate thereof.

2. The method of claim 1 wherein the inhibition of PDE7 to regulate T-cell function.

3. The method of claim 1 wherein, in Formula 1, $R_1$ is $NR_aR_b$ where $R_a$ or $R_b$ are hydrogen or lower alkyl;

$R_2$ is hydrogen, $C_{1-8}$alkyl or $C_{1-3}$alkyl-Ar, where Ar is phenyl unsubstituted or substituted by $C(O)OR_7$;

$R_3$ is $NO_2$, Cl, Br, or $NR_aR_b$ where $R_a$ and $R_b$ are independently H or $C_{1-6}$alkyl;

$R_4$ is hydrogen, —$OC_{1-6}$alkyl, Cl, $C(O)NR_aR_b$, $C_{1-4}$alkyl, —$OCHF_2$, —$CH_2OR_8$, —$OC_{1-3}$alkylAr where Ar is phenyl, unsubstituted or substituted by $C(O)OR_7$ or $CH_2NH(O)CH_3$;

$R_5$ is hydrogen;

$R_6$ is Cl, Br or methyl or a pharmaceutically acceptable salt thereof.

4. The method of claim 1 wherein a compound of Formula 1 is:

2-methyl-5-nitro(N,N-dimethyl)benzenesulfonamide;

2,4-dimethyl-5-nitro(N,N-dimethyl)benzenesulfonamide;

2-ethyl-5-nitro(N,N-dimethyl)benzenesulfonamide;

4-methoxy-2-methyl-5-nitro(N,N-dimethyl)benzenesulfonamide;

4-(3-carboxybenzyloxy)-2-methyl-5-nitro(N,N-dimethyl)benzenesulfonamide;

4-difluoromethoxy-2-methyl-5-nitro(N,N-dimethyl)benzenesulfonamide;

4-bromo-2-methyl-5-nitro(N,N-dimethyl)benzenesulfonamide;

4-amido-2-methyl-5-nitro(N,N-dimethyl)benzenesulfonamide;

4-methyleneoxy-2-methyl-5-nitro(N,N-dimethyl)benzenesulfonamide;

2-methyl-4-(methyl)methyleneoxy-5-nitro(N,N-dimethyl)benzenesulfonamide;

5-chloro-2-methyl(N,N-dimethyl)benzenesulfonamide;

4,5-dichloro-2-methyl(N,N-dimethyl)benzenesulfonamide;

2,4,5-trichloro-N,N-dimethyl)benzenesulfonamide;

2,5-dichloro-4-methoxy(N,N-dimethyl)benzenesulfonamide;

2,5-dichloro-4-difluoromethoxy(N,N-dimethyl)benzenesulfonamide;

5-bromo-2-methyl(N,N-dimethyl)benzenesulfonamide;

2-bromo-5-cyano(N,N-dimethyl)benzenesulfonamide;

3-N,N-dimethylamino-2-methyl(N,N-dimethyl)benzenesulfonamide.

* * * * *